US006574504B1

(12) United States Patent
Mazaury et al.

(10) Patent No.: US 6,574,504 B1
(45) Date of Patent: Jun. 3, 2003

(54) METHOD FOR COSMETIC TREATMENT OF THE SKIN AND THE SCALP USING ELECTROMAGNETIC WAVES AND ESSENTIAL OILS

(75) Inventors: André Mazaury, Saint Chamas (FR); Vincente Bellisi, Saint Chamas (FR)

(73) Assignee: BX3 General Labs, Clarens Montreux (CH)

( * ) Notice: Subject to any disclaimer, the term of this patent is extended or adjusted under 35 U.S.C. 154(b) by 0 days.

(21) Appl. No.: 09/743,856
(22) PCT Filed: Jul. 13, 1999
(86) PCT No.: PCT/FR99/01712
§ 371 (c)(1), (2), (4) Date: Mar. 7, 2001
(87) PCT Pub. No.: WO00/03762
PCT Pub. Date: Jan. 27, 2000

(30) Foreign Application Priority Data

Jul. 17, 1998 (FR) .............................................. 98 09522

(51) Int. Cl.⁷ .............................. A61N 1/40; A61N 2/02
(52) U.S. Cl. .............................. 607/3; 607/50; 607/155
(58) Field of Search .............................. 607/3, 50, 155; 128/898

(56) References Cited

U.S. PATENT DOCUMENTS 5,236,410 A * 8/1993 Granov et al. ................ 600/12
5,511,563 A * 4/1996 Diamond ..................... 607/88
5,817,089 A * 10/1998 Tankovich et al. ............. 606/9
6,267,720 B1 * 7/2001 Knox et al. .................. 600/15

FOREIGN PATENT DOCUMENTS

| EP | 0 497 672 A1 | 8/1992 | ............ A61N/1/40 |
| EP | 0 655 261 A2 | 5/1995 | ............ A61N/2/00 |
| FR | 2 454 817 | 11/1980 | ............ A61N/5/02 |
| FR | 2 665 366 | 2/1992 | ............ A61N/1/32 |
| FR | 2 706 131 | 12/1994 | ............ A61N/1/20 |
| WO | 94/21326 | 3/1994 | ............ A61N/1/32 |

* cited by examiner

Primary Examiner—Carl Layno
(74) Attorney, Agent, or Firm—Browdy and Neimark, P.L.L.C.

(57) ABSTRACT

A method for synergetic amplification of the standard effects of an essential oil with beneficent properties for the skin, the scalp, the nails and the hair, which consists in applying on the zone to be treated the desired essential oil or mixture of essential oils, and in subjecting said zone to the action of pulsed high frequency electromagnetic waves with frequency ranging between 1 MHz and 300 MHz, with a time spacing of 0.1 to 400 milliseconds between each wave impulse, and with a power of $10^{-6}$ W to 2 W, cosmetic treatment kit and pulsed athermal high frequency electromagnetic-wave generator with instructions for joint use to obtain amplified effects thereof.

17 Claims, 1 Drawing Sheet

Figure 1:
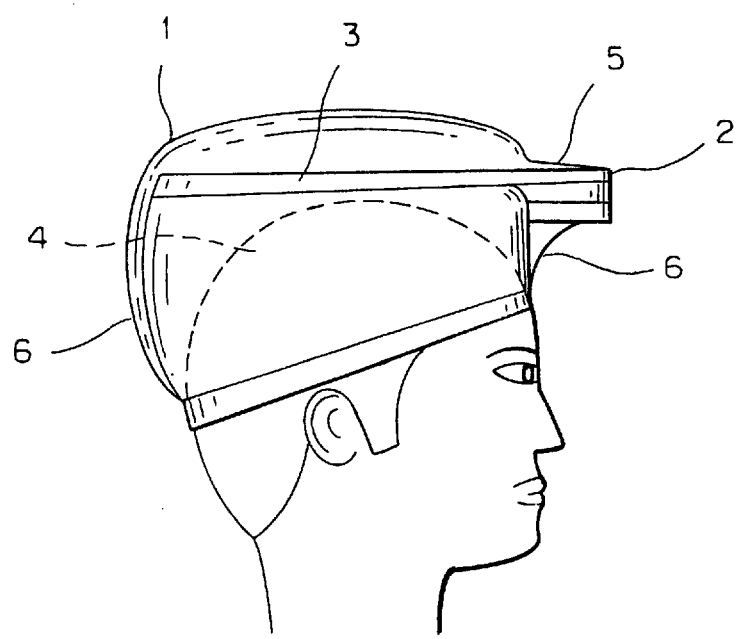

METHOD FOR COSMETIC TREATMENT OF THE SKIN AND THE SCALP USING ELECTROMAGNETIC WAVES AND ESSENTIAL OILS

The present application is the national stage under 35 U.S.C. 371 of PCT/FR99/01712, filed Jul. 13 1999.

The invention concerns a new cosmetic treatment of the skin, the scalp and their derivatives using pulsed high frequency electromagnetic waves with athermal effect and essential oils.

Traditionally, skin, scalp and hair problems are treated by all sorts of active principles, including, for example, allantoin, alpha-hydroxy acids, coaltar, and minoxidil, and available in a whole variety of galenical forms such as cremes, milks, lotions, water in oil or oil in water emulsions, shampoos etc.

Certain problems are also treated as described in FR-A-2 665 366. According to this document, a low-frequency current generating device is used, in contact with the skin at the site to be treated, producing an alternating current of a few millionths of an ampere in intensity, to carry out a micro-massage of the skin. The case of the device forms one electrode and the other electrode is applied to the user's skin, which closes the circuit to carry out the mechanical massage. According to this document, the electric massage by itself produces a cosmetic effect, as wrinkles would be reduced and the pores of the skin would be tightened; moreover, the products, cremes or essential oils, could penetrate more deeply into the skin and thus increase their action tenfold, as could a manual massage. These suppositions that an electric massage could replace a conventional manual massage are not however supported by any evidence.

These problems have also been treated by a number of pieces of equipment, including for example, lasers, devices delivering faradic or galvanic currents, devices delivering water vapour, or emitters of pulsed athermal high frequency electromagnetic waves as described in EP-0 497 672.

In particular, research is always being carried out into an effective method to combat hair loss. In fact, all the existing treatments, even the most recent, such as those based on minoxidil, have proved disappointing.

Now, following prolonged studies, the applicant has discovered that a treatment by pulsed high frequency electromagnetic waves with athermal effect used in accordance with certain parameters, considerably amplified, in an unexpected manner, a certain number of essential oils' own effects.

This is why the present invention has as its object a method for amplification with synergetic effect of the conventional effects of an essential oil with beneficent properties for the skin, the scalp, the nails and the hair, and pulsed high frequency electromagnetic waves, characterised in that the desired essential oil or the mixture of essential oils is applied on the zone to be treated and said zone is subjected to the action of pulsed high frequency electromagnetic waves, with frequency ranging between 1 MHz and 300 MHz, with a time spacing of 0.1 to 400 milliseconds between each wave impulse, and with a power of $10^{-6}$ W to 2 W.

The usable essential oils can be, for example, with regard to problems of hair loss, one or more essential oils chosen from the essential oils of bay St Thomas, birch, cade, camomile, cinnamon, cedar, cypress, geranium, laurel, lavender, orange, patchouli, pine, rosemary, sandalwood, sage, wild thyme, thuya, thyme, or ylang-ylang. The essential oils used in preference are bay St Thomas, birch, cade, cinammon, cedar, lemon, cypress, laurel, patchouli, rosemary, sandalwood, sage, thuya, thyme, or ylang-ylang, notably the essential oils of bay St Thomas, birch, cade, cinnamon, cedar, laurel, patchouli, rosemary, thuya, thyme, or ylang-ylang, and particularly the essential oils birch, cinnamon, cedar, laurel, patchouli, rosemary, thuya, thyme, or ylang-ylang.

For problems of cutaneous dermatoses, one or more essential oils can for example be used, chosen from the essential oils of spike lavender, basil, benzoin, bergamot, rosewood, birch, cade, cajeput, camomile, cinnamon, carrot, cedar, lemon, copaiba, cypress, elemi, eucalyptus, gaultheria, juniper, geranium, clove, gurjun, helichrysum, hyssop, laurel, lavender, lavandin, marjoram, melissa, myrrh, myrtle, niaouli, bitter orange, orange, oregano, palmarosa, patchouli, pine, rosemary, rose, sandalwood, savory, sassafras, sage, wild thyme, styrax, thuya, thyme, vetiver, ylang-ylang and Canada balsam, balsam of Peru and balsam of Tolu. The essential oils used in preference are those of benzoin, rosewood, birch, cade, cajeput, camomile, carrot, cedar, lemon, copaiba, geranium, clove, gurjun, laurel, lavender, marjoram, myrtle, niaouli, oregano, palmarosa, patchouli, sandalwood, sage and balsam of Peru, notably the essential oils of benzoin, rosewood, cade, cajeput, carrot, cedar, lemon, copaiba, geranium, clove, gurjun, lavender, marjoram, niaouli, palmarosa, patchouli and sage, and particularly essential oils of benzoin, rosewood, cade, carrot, geranium, lavender, marjoram, niaouli, patchouli and sage.

For problems of wrinkles, one or more essential oils can for example be used, chosen from the essential oils of bitter almond, spike lavender, basil, benzoin, rosewood, cade, cajeput, camomile, cinnamon, carrot, cedar, lemon, copaiba, cypress, elemi, eucalyptus, juniper, geranium, clove, helichrysum, hyssop, lavender, lime, mace, nutmeg, niaouli, bitter orange, orange, oregano, palmarosa, grapefruit, patchouli, rosemary, rose, sandalwood, savory, sage, thyme, ylang-ylang, et Canada balsam, balsam of Peru and balsam of Tolu. The essential oils used in preference are basil, benzoin, rosewood, cajeput, camomile, carrot, cedar, cypress, geranium, lavender, niaouli, bitter orange, oregano, palmarosa, patchouli, rosemary, sandalwood, sage, thyme and ylang-ylang, notably basil, rosewood, cajeput, camomile, carrot, cypress, geranium, lavender, niaouli, bitter orange, palmarosa, patchouli, rosemary, sage, thyme and ylang-ylang and particularly basil, rosewood, carrot, cypress, geranium, lavender, bitter orange, palmarosa, patchouli, rosemary, sage and thyme.

For problems of reddened skin, one or more essential oils for example can be used, chosen from the essential oils of bitter almond, spike lavender, basil, benzoin, rosewood, cade, cajeput, camomile, cinnamon, carrot, cedar, lemon, copaiba, cypress, elemi, eucalyptus, juniper, geranium, clove, helichrysum, hyssop, lavender, lime, mace, nutmeg, niaouli, bitter orange, orange, oregano, palmarosa, grapefruit, patchouli, rosemary, rose, sandalwood, savory, sage, thyme and ylang-ylang and Canada balsam, balsam of Peru and balsam of Tolu. The essential oils used in preference are those of benzoin, rosewood, camomile, carrot, cedar, lemon, cypress, geranium, helichrysum, lavender, niaouli, bitter orange, oregano, palmarosa, patchouli, rosemary, rose, sandalwood, sage, thyme and ylang-ylang and balsam of Peru, notably benzoin, rosewood, camomile, carrot, cedar, lemon, cypress, geranium, helichrysum, lavender, bitter orange, palmarosa, patchouli, rosemary, sage and thyme, especially rosewood, carrot, cedar, lemon, cypress, helichrysum, lavender, bitter orange, palmarosa, patchouli, rosemary, sage and thyme and particularly rosewood, cedar, lemon, cypress, helichrysum, lavender, bitter orange, palmarosa, patchouli, rosemary, sage and thyme.

For breast problems, as for firming of the bust, one or more essential oils can be used, for example chosen from the essential oils of bitter almond, spike lavender, basil, benzoin, rosewood, cade, cajeput, camomile, cinnamon, carrot, cedar, lemon, copaiba, cypress, elemi, eucalyptus, juniper, geranium, clove, helichrysum, hyssop, lavender, lime, mace, nutmeg, niaouli, bitter orange, orange, oregano, palmarosa, grapefruit, patchouli, rosemary, rose, sandalwood, savory, sage, thyme, and ylang-ylang and Canada balsam, balsam of Peru and balsam of Tolu. The essential oils used in preference are those of bitter almond, benzoin, rosewood, camomile, carrot, cedar, lemon, cypress, eucalyptus, clove, hyssop, lavender, lime, mace, nutmeg, bitter orange, oregano, palmarosa, patchouli, rosemary, sandalwood, sage, notably bitter almond, rosewood, carrot, cedar, lemon, cypress, eucalyptus, clove, hyssop, lime, mace, nutmeg, bitter orange, palmarosa, patchouli, rosemary, sandalwood, sage and particularly bitter almond, rosewood, cedar, lemon, eucalyptus, clove, hyssop, lime, mace, nutmeg, bitter orange, palmarosa, rosemary and sandalwood.

These essential oils, which are preferably natural, can be used pure or diluted for example in vegetable oils, notably musk rose, sesame, safflower, soya, sunflower, grape seed, wheatgerm, olive, evening primrose or borage. Dilution may be as much as ½, 1/4, 1/10, or even 1/20. Low concentrations such as 5 or 10%, or even 30%, are preferably used for zones where the skin is sensitive and strong concentrations for zones such as non-irritated scalp. It is advantageous to combine 4 to 20 essential oils and preferably 6 to 15 essential oils.

These essential oils are now available commercially and can be obtained for example from the company ADRIAN in Marseilles (France), or COOPER at Melun (France).

The vegetable oils can be obtained for example from the company SICTIA in Marseilles.

The above pulsed high frequency electromagnetic waves with athermal effect can be obtained for example by using the device described in EP-A-0 497 672.

The emission power of the wave generator may range for example from $10^{-6}$ W to 2 W. In the case of direct and localised application to the zone to be treated, a power of for example 0.2 to 1 mW may be sufficient. The emission power is preferably distributed uniformly over the surface of the zone to be treated.

Under preferential conditions of realisation, the emission of the waves is achieved by using one or more antennae fitted onto a device serving as support the antenna or antennae, said antennae being separated from the zone to be treated by at least 50 cm, preferably 0.5 to 15 cm, notably 1 to 5 cm, and particularly 1.5 to 3 cm. It is thus for example that in the case of a portable emitter that the antenna or antennae will be separated from the zone to be treated by means of, for example, a system of spacers separating the antenna from the zone to be treated, and taking support for example at the outside of the zone to be treated. This is why for example, in the treatment of baldness, a helmet can notably be used, supported at the level of the forehead and on the nape of the neck (these supports constituting the system of spacers), the helmet serving as support for one or more antennae separated from the cranium.

The shape of the antenna may be for example flat as shown below in the experimental part, but under other preferential conditions, the shape of the antenna corresponds to that of the zone to be treated so as to transmit a regular emission of electromagnetic waves to all the said zone. It should be noted that the absence of contact with the zone to be treated makes it possible to avoid the risks of electrocution.

The surface of the antenna or antennae may be for example 10 to 600 cm$^2$, but under preferential conditions the surface ranges from 50 to 300 cm$^2$.

The number of antennae of the same emitter can be for example 1 to 9 but under preferential conditions, this number will be from 1 to 4. It is of course possible to use numerous individual antennae, for example 10 to 20 with a small area, notably to confine the emission only to the desired site, the other antennae remaining inactive.

The emission frequency can be for example from 1 to 300 MHz, but under preferential conditions, the emission frequency ranges from 6 to 50 MHz.

The time spacing between two impulses can be for example from 0.1 to 200 ms, but under preferential conditions this time spacing can be 0.4 to 200 ms.

The duration of an impulse can be for example from 0.1 to 200 ms, but under preferential conditions this duration is from 0.4 to 200 ms.

Under preferential conditions for implementation of the method described above, the duration of an impulse and the time spacing between two impulses are identical, which simplifies the construction.

The emission can be for example from $10^{-6}$ W to 2 W, but under preferential conditions the emission intensity is from 0.2 to 1 mW.

The emission of the waves over the zone to be treated is preferably effected less than 72 hours after application of essential oils, notably less than 3 hours, particularly less than 1 hour, and especially just after application of the essential oils.

According to the applicant's studies, the properties of the essential oils notably the antiseptic, bacteriostatic, bactericidal, antiviral, anti-mycosic, healing, stimulating and balance-restoring, functional, catalytic, bio-psychic, and physical properties would result from their ability to give or receive electronic energy due to their molecular structure. In fact, the waves constitute a means of locomotion of the vibratory energy of its two components, electric and magnetic. Now, the pulsed high frequency electromagnetic waves with athermal effect would prepare the action of the essential oils by acting on the receptivity of the cells, and in addition by favouring the receptivity and the ability to emit molecules, notably aromatic molecules present in the essential oils, thus producing a synergy of unexpected effects.

The method according to the invention thus makes it possible to considerably amplify the effects of the essential oils used separately.

It therefore finds its application notably in various cosmetic treatments based on essential oils, well known from the state of the art.

The present application also has as its object a cosmetic treatment kit for the skin, the scalp and their derivatives, for implementation of the above method, characterised in that it includes one or more mixtures of essential oils, and a pulsed athermal high frequency electromagnetic-wave generator, notably capable of emitting waves having the above characteristics, possibly with instructions for joint use with essential oils to obtain amplified effects thereof. This generator may be of a portable type as shown below in the experimental part, or of the "professional" type, i.e. installed on a support as described in EP-A-0 497 672.

The present application also has as its object a pulsed athermal high frequency electromagnetic-wave generator notably corresponding to the above characteristics, with instructions for joint use with essential oils to obtain amplified effects thereof (with synergetic effect), as well as use of pulsed athermal electromagnetic waves to obtain amplified effects (with synergetic effect) of essential oils.

The present application finally has as its object a method for treatment of hair loss problems, a method for treatment of problems of cutaneous dermatoses within the scope of cosmetics, a method for treatment of problems of wrinkles, a method for treatment of problems of reddened skin, a method for treatment of breast problems as for firming of the bust, in which pulsed athermal high frequency electromagnetic waves are used to obtain amplified effects (with synergetic effect), of essential oils.

The following examples illustrate the invention.

FIG. 1 schematically represents a side view in elevation and partial section of a portable helmet emitting pulsed high frequency waves fitted on the cranium of an individual.

Figure 2:
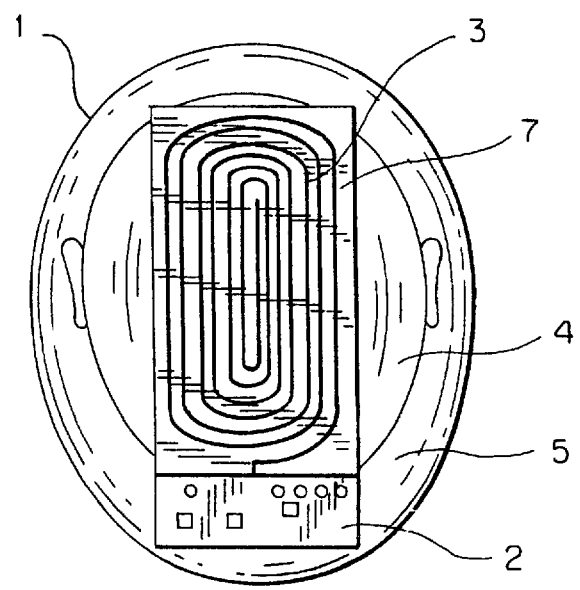

FIG. 2 is a schematic view from above of a helmet emitter as in FIG. 1, exploded at the level of the antenna.

On FIG. 1, it is possible to observe the helmet 1 serving as support for an antenna emitter 3 of flat shape, and constituted by the spirally printed circuit board placed at a distance of 1 cm to several centimeters from the cranium. This helmet 1 includes the control box 5 in which the electronic part 2 is situated and a battery and on the surface buttons for the selection of frequency, power, timing and starting up. The antenna 3 is separated from the cranium 4 by means of the lower sides 6 of the helmet serving as spacers.

On FIG. 2, it is possible to see more particularly the spiral design of antenna 3 on its printed circuit 7 which is an integral part of the helmet, and the selection buttons The printed circuit has a width of approximately 10 cm. The antenna is spiral and comprises approximately 20 single turns.

The absence of contact between the antenna and the zone to be treated makes it possible to avoid the risks of electrocution.

EXAMPLE 1

Mixture of Essential Oils for the Treatment of Hair Loss

| Essential oils | Percentage |
| --- | --- |
| Birch | 6.67 |
| Cinnamon | 13.33 |
| Cedar | 13.33 |
| Laurel | 13.33 |
| Patchouli | 5.00 |
| Rosemary | 6.67 |
| Thuya | 25.00 |
| Thyme | 10.00 |
| Ylang-ylang | 6.67 |
| TOTAL | 100% |

EXAMPLE 2

Mixture of Essential Oils Diluted for Cosmetic Treatment of Dermatoses

| Essential oils | Percentage | Vegetable oils | Percentage |
| --- | --- | --- | --- |
| Benzoin | 5.00 | Olive | 16.67 |
| Rosewood | 3.33 | Sesame | 16.67 |
| Cade | 3.33 | Safflower | 16.67 |
| Carrot | 5.00 | | |
| Geranium | 5.00 | | |
| Lavender | 6.67 | | |
| Marjoram | 3.33 | | |
| Niaouli | 5.00 | | |
| Patchouli | 6.67 | | |
| Sage | 6.67 | | |
| TOTAL | 50% | TOTAL | 50% |

EXAMPLE 3

Mixture of Essential Oils Diluted for the Cosmetic Treatment of Reddened Skins

| Essential oils | Percentage | Vegetable oils | Percentage |
| --- | --- | --- | --- |
| Rosewood | 0.67 | Borage | 11.0 |
| Cedar | 2.00 | Wheat germ | 12.0 |
| lemon | 1.33 | Safflower | 11.0 |
| Cypress | 2.67 | Soya | 11.0 |
| Helichrysum | 2.67 | Sunflower | 11.0 |
| Lavender | 1.33 | Grape seed | 24.0 |
| Bitter orange | 1.33 | | |
| Palmarosa | 2.67 | | |
| Patchouli | 2.00 | | |
| Rosemary | 2.00 | | |
| Sage | 0.67 | | |
| Thyme | 0.67 | | |
| TOTAL | 20% | TOTAL | 80% |

EXAMPLE 4

Mixture of Essential Oils Diluted for the Cosmetic Treatment of Wrinkles

| Essential oils | Percentage | Vegetable oils | Percentage |
| --- | --- | --- | --- |
| Basil | 1.33 | Evening primrose | 11.0 |
| Rosewood | 1.33 | Musk rose | 11.0 |
| Carrot | 2.00 | Safflower | 11.0 |
| Cypress | 1.33 | Sesame | 11.0 |
| Geranium | 1.33 | Wheat germ | 12.0 |
| Lavender | 1.33 | Grape seed | 24.0 |
| Bitter orange | 2.00 | | |
| Palmarosa | 2.70 | | |
| Patchouli | 2.00 | | |
| Rosemary | 2.00 | | |
| Sage | 1.33 | | |
| Thyme | 1.33 | | |
| TOTAL | 20% | TOTAL | 80% |

EXAMPLE 5

Mixture of Essential Oils Diluted for Firming of the Breasts

| Essential oils | Percentage | Vegetable oils | Percentage |
| --- | --- | --- | --- |
| Bitter almond | 2.50 | Grape seed | 22.40 |
| Rosewood | 0.84 | Wheat germ | 13.15 |
| Cedar | 1.66 | Safflower | 13.15 |
| Lemon | 1.66 | Soya | 13.15 |
| Eucalyptus | 2.50 | Sunflower | 13.15 |
| Clove | 1.66 | | |
| Hyssop | 2.50 | | |
| Lime | 0.84 | | |
| Mace | 0.84 | | |
| Nutmeg | 1.66 | | |
| Bitter orange | 0.84 | | |
| Palmarosa | 3.34 | | |
| Rosemary | 1.66 | | |
| Sandalwood | 2.50 | | |
| TOTAL | 25% | TOTAL | 75% |

EXAMPLE 6

Demonstration of the Combined Effect of the Mixture of Essential Oils in Example 1 and Pulsed High Frequency Electromagnetic Waves with Athermal Effect A group of 30 persons was formed, presenting hair loss of androgenetic type, and in whom the area of the bald patch ranged from 0 to 80 cm². A first third of these persons was subjected to a conventional manual massage of the zone to be treated with 0.5 ml of the mixture of essential oils in example 1 three times a week for three months.

A second third was subjected to a treatment for half-an-hour, using the helmet described in FIGS. 1 and 2, twice a week for three months. The emission of the helmet corresponded to the following characteristics:

Area of the antenna 200 cm²

Emission frequency: 10 MHz

Time spacing between two impulses: 0.625 ms

Duration of one impulse : 0.625 ms power: 1 mW

Average time spacing between the antennae and the zone to be treated: 2 cm.

The last third was subjected to the above treatment based on essential oils, followed, 1 minute afterwards, by the above treatment based on pulsed athermal high frequency electromagnetic waves.

The results obtained are as follows:

1st third: arrest of abnormal loss and improvement in the quality of the hair in 70% of cases at the end of a month with appearance of down in 10% of cases at the end of three months.

2nd third: improvement in the quality of the hair, stabilisation of abnormal loss in 50% of cases at the end of two months.

3rd third: arrest of abnormal loss and improvement in the quality of the hair in 80% of cases at the end of a month with regrowth in 50% of cases at the end of two months.

The synergy of the effects shows positive results which are more numerous and more rapid, on the arrest of the loss and improvement of the hair:

80% instead of 70% with essential oils alone and 50% with the waves alone;

1 month instead of 2 with the waves alone regrowth:

50% instead of 10% with the essential oils alone and 0% with the waves alone;

2 months instead of 3 with the essential oils alone

Moreover the hair that regrows does not remain at the stage of down.

EXAMPLE 7

Demonstration of the Combined Effect of the Mixture of Essential Oils in Example 1 and Pulsed Athermal High Frequency Electromagnetic Waves A group of 50 persons was taken presenting hair loss of androgenetic type, and in whom the area of the bald patch ranged from 0 to 80 cm², who were subjected to the above combined treatment.

An improvement could be observed in 41 persons at the end of one month of treatment. This improvement in quality was characterised by thickening of the hairs, reduction in and even disappearance of the pellicular condition and/or the hyperseborrhea at the origin of the hair loss and an arrest of excessive loss. After two months of treatment, a regrowth of the hair was observed in approximately 50% of cases.

Confirmation was thus obtained of the results already obtained, demonstrating the undeniable complementarity of the combination of essential oils—pulsed high frequency electromagnetic waves on the arrest of excessive loss, improvement of the hair and regrowth.

EXAMPLE 8

Treatment of Dermatoses of the Scalp of Eczematous Type

A certain number of problems of dermatosis of the scalp of the eczematous type were treated by the method indicated in example 6, but using the mixture of essential oils in example 2, and treating for half-an-hour three times a week using electromagnetic waves and applying the mixture of essential oils every day for three months.

From the first sessions, a clear improvement was observed, with total disappearance in 37 of the persons at the end of twenty days.

This type of problem being often linked to psychosomatic phenomena and possibly returning in the case of stress, these treatments must be pursued or resumed as soon as the symptoms reappear, to make them disappear very rapidly.

What is claimed is:

1. A method for amplification with synergetic effect of the standard effects of an essential oil with beneficent properties for the skin, the scalp, the nails and the hair, and of pulsed high frequency electromagnetic waves, characterised in that the desired essential oil or mixture of essential oils are applied to the zone to be treated, and said zone is subjected to the action of athermic pulsed high frequency electromagnetic waves, with a frequency ranging between 1 MHz and 300 MHz, with a time spacing of 0.1 to 400 milliseconds between each wave impulse, and with a power of $10^{-6}$ W to 2 W.

2. A method according to claim 1, characterised in that the emission of the wave generator used ranges between 0.2 and 1 mW.

3. A method according to claim 1, characterised in that cosmetic problems of cutaneous dermatoses are treated using one or more essential oils chosen from the essential oils of spike lavender, basil, benzoin, bergamot, rosewood, birch, cade, cajeput, camomile, cinnamon, carrot, cedar, lemon, copaiba, cypress, elemi, eucalyptus, gaultheria, juniper, geranium, clove, gurjun, helichrysum, hyssop, laurel, lavender, lavandin, marjoram, melissa, myrrh, myrtle, niaouli, bitter orange, orange, oregano, palmarosa, patchouli, pine, rosemary, rose, sandalwood, savory, sassafras, sage, wild thyme, styrax, thuya, thyme, vetiver, ylang-ylang and Canada balsam, balsam of Peru and balsam of Tolu.

4. A method according to claim 1, characterised in that problems of wrinkles are treated using one or more essential oils chosen from the essential oils of bitter almond, spike lavender, basil, benzoin, rosewood, cade, cajeput, camomile, cinnamon, carrot, cedar, lemon, copaiba, cypress, elemi, eucalyptus, juniper, geranium, clove, helichrysum, hyssop, lavender, lime, mace, nutmeg, niaouli, bitter orange, orange, oregano, palmarosa, grapefruit, patchouli, rosemary, rose, sandalwood, savory, sage, thyme, ylang-ylang, Canada balsam, balsam of Peru and balsam of Tolu.

5. A method according to claim 1, characterised in that problems of reddened skin are treated, using one or more essential oils chosen from the essential oils of bitter almond, spike lavender, basil, benzoin, rosewood, cade, cajeput, camomile, cinnamon, carrot, cedar, lemon, copaiba, cypress, elemi, eucalyptus, juniper, geranium, clove, helichrysum, hyssop, lavender, lime, mace, nutmeg, niaouli, bitter orange, orange, oregano, palmarosa, grapefruit, patchouli, rosemary, rose, sandalwood, savory, sage, thyme and ylang-ylang Canada balsam, balsam of Peru and balsam of Tolu.

6. A method according to claim 1, characterised in that problems of the breasts are treated, as for firming of the bust, using one or more essential oils chosen from the essential oils of bitter almond, spike lavender, basil, benzoin, rosewood, cade, cajeput, camomile, cinnamon, carrot, cedar, lemon, copaiba, cypress, elemi, eucalyptus, juniper, geranium, clove, helichrysum, hyssop, lavender, lime, mace, nutmeg, niaouli, bitter orange, orange, oregano, palmarosa, grapefruit, patchouli, rosemary, rose, sandalwood, savory, sage, thyme, and ylang-ylang and Canada balsam, balsam of Peru and balsam of Tolu.

7. The method of claim 1 wherein the emission frequency ranges from 6 to 50 MHz.

8. The method of claim 1 wherein the time spacing between each wave impulse is 0.1 to 200 ms.

9. The method according to claim 1 wherein the time spacing between each wave impulse is 0.4 to 200 ms.

10. The method of claim 1 wherein the duration of an impulse is from 0.1 to 200 ms.

11. The method of claim 1 wherein the duration of an impulse is from 0.4 to 200 ms.

12. A method for amplification with synergetic effect of the standard effects of an essential oil with beneficent properties for the skin, the scalp, the nails and the hair, and of pulsed high frequency electromagnetic waves, characterised in that the desired essential oil or mixture of essential oils are applied to the zone to be treated, and said zone is subjected to the action of pulsed high frequency electromagnetic waves, with a frequency ranging between 1 MHz and 300 MHz, with a time spacing of 0.1 to 400 milliseconds between each wave impulse, and with a power of $10^{-6}$ W to 2 W and in that the emission of the waves is achieved of one or more antennae fitted onto a device serving as a support for the antenna or antennae, said antennae being separated from the zone to be treated by between 0.5 and 15 cm.

13. A method according to claim 12, characterised in that the area of the antenna or antennae ranges between 50 and 300 cm$^2$.

14. A method for amplification with synergetic effect of the standard effects of an essential oil with beneficent properties for the skin, the scalp, the nails and the hair, and of pulsed high frequency electromagnetic waves, characterised in that the desired essential oil or mixture of essential oils are applied to the zone to be treated, and said zone is subjected to the action of pulsed high frequency electromagnetic waves, with a frequency ranging between 1 MHz and 300 MHz, with a time spacing of 0.1 to 400 milliseconds between each wave impulse, and with a power of $10^{-6}$ W to 2 W and in that the emission of the waves is effected less than 3 hours after the application of the essential oils.

15. A method for amplification with synergetic effect of the standard effects of an essential oil with beneficent properties for the skin, the scalp, the nails and the hair, and of pulsed high frequency electromagnetic waves, characterised in that the desired essential oil or mixture of essential oils are applied to the zone to be treated, and said zone is subjected to the action of pulsed high frequency electromagnetic waves, with a frequency ranging between 1 MHz and 300 MHz, with a time spacing of 0.1 to 400 milliseconds between each wave impulse, and with a power of $10^{-6}$ W to 2 W and in that problems of hair loss are treated using one or more essential oils of bay St Thomas, birch, cade, camomile, cinnamon, cedar, lemon, cypress, geranium, laurel, lavender, orange, patchouli, pine, rosemary, sandalwood, sage, wild thyme, thuya, thyme, or ylang-ylang.

16. A kit for cosmetic treatment of the skin, scalp and their derivatives, characterised in that it includes one or more mixtures of essential oils, and a pulsed athermal high frequency electromagnetic-wave generator capable of emitting a frequency ranging between 1 MHz and 300 MHz, with a time spacing of 0.1 to 400 milleseconds between each wave impulse, with a power of $10^{-6}$ W to 2 W.

17. A kit for cosmetic treatment of the skin, scalp and their derivatives, characterised in that it includes one or more mixtures of essential oils, a pulsed athermal high frequency electromagnetic-wave generator capable of emitting a frequency ranging between 1 MHz and 300 MHz, with a time spacing of 0.1 to 400 milliseconds between each wave impulse, with a power of $10^{-6}$ W to 2 W, and instructions for joint use with essential oils to obtain amplified effects thereof.

* * * * *